US006922587B2

(12) United States Patent
Weinberg

(10) Patent No.: US 6,922,587 B2
(45) Date of Patent: Jul. 26, 2005

(54) SYSTEM AND METHOD FOR TRACKING PROGRESSION OF LEFT VENTRICULAR DYSFUNCTION USING IMPLANTABLE CARDIAC STIMULATION DEVICE

(75) Inventor: Lisa P. Weinberg, Moorpark, CA (US)

(73) Assignee: Pacesetter, Inc., Sylmar, CA (US)

(*) Notice: Subject to any disclaimer, the term of this patent is extended or adjusted under 35 U.S.C. 154(b) by 322 days.

(21) Appl. No.: 10/183,243

(22) Filed: Jun. 26, 2002

(65) Prior Publication Data

US 2004/0002741 A1 Jan. 1, 2004

(51) Int. Cl.[7] .............................................. A61N 1/362
(52) U.S. Cl. ............................................. 607/9; 607/17
(58) Field of Search ..................... 607/3, 9, 14, 16–19, 607/23–25; 600/509, 513, 515–516

(56) References Cited

U.S. PATENT DOCUMENTS

| | | | |
|---|---|---|---|
| 4,252,124 A | 2/1981 | Maurer et al. .............. | 128/635 |
| 4,436,092 A | 3/1984 | Cook et al. ................. | 128/419 |
| 4,527,568 A | 7/1985 | Rickards ..................... | 128/419 |
| 4,535,774 A | 8/1985 | Olson ......................... | 128/419 |
| 4,759,366 A | 7/1988 | Callaghan ................... | 128/419 |
| 5,042,497 A | 8/1991 | Shapland .................... | 128/696 |
| 5,213,098 A | 5/1993 | Bennett et al. ............. | 128/419 |
| 5,275,171 A | 1/1994 | Barcel ........................ | 607/122 |
| 5,476,483 A | 12/1995 | Bornzin et al. ............. | 607/17 |
| 5,480,412 A | 1/1996 | Mouchawar et al. ........ | 607/6 |
| 5,527,344 A | 6/1996 | Arzbaecher et al. ......... | 607/3 |
| 6,128,534 A | 10/2000 | Park et al. ................... | 607/17 |
| 6,129,744 A * | 10/2000 | Boute ......................... | 607/25 |
| 6,190,324 B1 * | 2/2001 | Kieval et al. ................ | 600/483 |
| 6,804,555 B2 * | 10/2004 | Warkentin ................... | 607/9 |
| 2003/0171782 A1 * | 9/2003 | Florio et al. ................. | 607/19 |

* cited by examiner

Primary Examiner—Carl Layno

(57) ABSTRACT

The progression or regression of left ventricular dysfunction (LVD) is automatically evaluated by a pacemaker or other implantable cardiac stimulation device by tracking changes in the resting sinus rate of the patient in which the device is implanted. The resting sinus rate is detected by first determining whether the patient is in a state of profound rest, such as sleep, then measuring the actual sinus rate during profound rest. Profound rest may be detected by using an activity variance sensor. An increase in the profound rest sinus rate over a period of several months indicates progression of LVD; whereas a decrease indicates regression. Appropriate LVD diagnostic information is recorded for subsequent review by a physician. Based on the progression or regression of LVD, the physician may then modify LVD drug therapy administered to the patient or may adjust control parameters of the pacemaker, such as overdrive pacing control parameters or control parameters affecting heart contractility via post-extrasystolic potentiation. If a drug pump is implanted within the patient for automatically delivering LVD drug therapy, the pacemaker controls the drug pump in view of any detected progression or regression of LVD. The technique may also be used to verify the efficacy of LVD drug therapy administered to the patient, whether delivered via an implanted drug pump or otherwise. Processing may be primarily performed within the implanted device itself or with an external programmer in communication with the implanted device. Activity state-based LVD tracking techniques are also set forth.

24 Claims, 10 Drawing Sheets

SYSTEM AND METHOD FOR TRACKING PROGRESSION OF LEFT VENTRICULAR DYSFUNCTION USING IMPLANTABLE CARDIAC STIMULATION DEVICE

FIELD OF THE INVENTION

The invention relates generally to a technique for use by an implantable cardiac stimulation device for tracking the progression or regression of left ventricular dysfunction (LVD).

BACKGROUND OF THE INVENTION

LVD is a heart condition wherein the left ventricle exhibits decreased functionality. Diagnostic measurements indicative of LVD include a diminished ejection fraction and a depressed level of motility of the left ventricular wall. Hence, the ability of the stroke volume of the heart to respond to exercise is limited and a degenerative reduction in cardiac output occurs. With LVD, the heart typically attempts to increase cardiac output primarily with an increase in heart rate. Patients with LVD have an increased risk for thromboembolic events, with a significant percentage of these patients dying from such events. LVD can also lead to congestive heart failure or myocardial infarction, among other cardiovascular diseases.

Accordingly, it would be highly desirable to provide a reliable technique for detecting the onset of LVD within patients and for tracking its progression. Many patients who are significantly at risk of LVD have already had a pacemaker or implantable cardioverter defibrillator (ICD) implanted for other reasons and so it would be beneficial to configure such implantable devices to detect and track the progression of LVD as well.

One technique proposed for detecting LVD using a pacing system is set forth in U.S. Pat. No. 6,129,744 to Boute. Briefly, sensed cardiac signals are utilized to evaluate LVD. In one example described therein, changes in the rest heart rate of the patient are monitored to detect trends indicating possible LVD. When LVD is indicated, the pacing system responds by altering the pacing rate in an attempt to be more responsive to patient exercise, initiating 3- or 4-chamber pacing or administering drug therapy.

Insofar as the detection of the rest heart rate is concerned, however, the technique described by Boute does not directly determine the rest rate but instead attempts to approximate the rest rate by extrapolating from trend curves or by determining the minimum rate of a twenty-four hour period. Hence, the technique of Boute may not properly determine the true rest rate and any conclusions drawn regarding LVD from the approximated rest rates may be inaccurate or erroneous, possibly triggering an improper change in pacing rate, an improper switch to a different pacing mode or the improper administration of drug therapy.

Accordingly, it would be desirable to provide an improved technique for detecting and tracking LVD using a pacing system or other implantable cardiac stimulation device, which more accurately and reliably detects the true rest rate, and it is to this end that aspects of the invention are drawn.

Once LVD is detected, drug therapy is typically administered, often using beta-blockers, angiotensin-converting enzyme inhibitors (ACEIs), diuretics, diltiazem, diltiazem, or angiotensin II antagonists. It would also be desirable to provide a technique for automatically evaluating the efficacy of such therapy using an implantable cardiac stimulation device and it is to this end that other aspects of the invention are drawn. It would also be desirable provide improved non-drug therapy for responding to LVD and further aspects of the invention are drawn to such therapy.

In circumstances where the implantable device may not have sufficient resources to perform full LVD tracking or full LVD drug efficacy evaluation, it would be desirable to instead configure the implantable device to transmit raw data to an external programmer configured to analyze the data and evaluate LVD progression and LVD drug efficacy. It is to this end that still further aspects of the invention are drawn.

SUMMARY OF THE INVENTION

In accordance with a first aspect of the invention, a technique is provided for tracking the progression or regression of LVD using an implantable cardiac stimulation device. The implantable device has a profound rest detector, a sinus rate detector and an LVD tracking unit or other control unit. The profound rest detector determines when the patient is in a state of profound rest, such as sleep. The sinus rate detector directly measures the sinus rate of the patient while at profound rest. The LVD tracking unit tracks changes in LVD, if any, within the patient based on changes in sinus rates measured while at profound rest.

In one example, the profound rest detector determines when the patient is asleep based on signals received from one or more sensors that detect a diurnally-varying parameter, such as sensors for detecting activity variance, body temperature, pH, blood $O_2$, heart rate variance, QT intervals, contractility, stroke volume or heart wall displacement. In one embodiment, three or more sinus rate values are detected about an hour apart and averaged so as to get a more accurate measurement. Other ways of averaging are possible. Progression or regression of LVD is determined by comparing the averaged sinus rate measured during sleep against a baseline sinus rate. The baseline rate may be, for example, the sinus rate of the patient as measured during sleep immediately following implantation of the device. If significant progression of LVD is detected, warning signals or other diagnostic information are transmitted to a bedside monitor or are recorded within the implantable device for subsequent transmission to an external programmer. During a follow-up session with the patient, a physician may then review the diagnostic information and, in particular, review any LVD progression warnings recorded therein. If warranted, the physician may then initiate or modify LVD drug therapy or adjust control parameters of the implantable device to reflect any progression or regression in LVD.

In another example, pacing therapy delivered to the patient by the implantable device is automatically modified based on any detected progression or regression in LVD. If LVD has been found to have progressed, the device is automatically controlled, for example, to switch to bi-ventricular pacing from single-site pacing, adjusting V—V timing, or, if overdrive pacing is being performed, the device is controlled to lower the aggressiveness of the overdrive pacing. Steps may be taken to increase heart contractility so as to increase stroke volume. If an internal drug pump or other drug dispensing device is provided along with the implantable device, the drug pump may be controlled to begin delivering LVD drugs to the patient or, if already doing so, to increase the dosage. The efficacy of LVD drug therapy may also be evaluated based on changes, if any, in the sinus rate measured while the patient is asleep.

Thus the first aspect of the invention provides an efficient technique for tracking LVD within patients using an implantable cardiac stimulation device. An important advantage of the technique is that it directly detects the profound rest sinus rates, rather than attempting to approximate the rate extrapolating from trend curves or by merely taking the medium rate detected over the previous twenty-four hours, and hence can achieve a more accurate and reliable evaluation of LVD progression. Moreover, the technique can be implemented using components already employed within many state-of-the-art implantable devices. Such devices typically include activity variance sensors or other sensors for use in detecting when the patient is asleep for the purposes of controlling the delivery of therapy. Hence, the LVD tracking technique can be implemented without requiring any significant additional resources. Moreover, the LVD tracking operations are performed primarily while the patient is asleep, so as not to further burden the microcontroller of the device during waking hours wherein more cardiac stimulation therapy is typically required. Additionally, various steps are automatically taken to address the progression of LVD, such as pacing to alter heart contractility, adjusting the aggressiveness of overdrive pacing or controlling the delivery of LVD drug therapy. Although there are many advantages to tracking LVD based on sinus rates detected at profound rest, LVD may alternatively be tracked by monitoring changes in sinus rates detected while the patient is within a predetermined activity state, such as an exercise state.

In accordance with a second aspect of the invention, an external programmer is configured to receive and display diagnostic information generated by an implantable cardiac stimulation device, which is representative of changes, if any, in LVD. The external programmer includes a telemetry unit, a display device and an LVD. The telemetry unit receives signals from the implantable device representative of the changes, if any, in LVD within the patient derived from sinus rates detected at profound rest. The display unit then displays diagnostic information representative of changes, if any, in LVD. Alternatively, the external programmer is configured to receive the sinus rates measured at profound rest by the implantable device and to track changes, if any, in LVD based on the received sinus rates. In other words, the implantable device measures the sinus rates at profound rest and the external device processes the sinus rates to track progression or regression in LVD. Likewise, the external programmer may be configured to evaluate the efficacy of LVD drug therapy based on sinus rate value received from the implanted device and to automatically recommend changes to the drug pump control parameters or to pacing control parameters, including heart rate contractility altering control parameters and overdrive pacing control parameters. Alternatively, the external programmer operates based on LVD diagnostic information generated by the implanted device while the patient is in a predetermined activity state, such as while exercising.

Thus various techniques are provided for tracking LVD using an implantable cardiac stimulation device or external programmer and for automatically adjusting therapy provided by the implanted device or for automatically evaluating the efficacy of LVD drug therapy. Other objects, features and advantages of the invention will be apparent from the detailed description to follow.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

Figure 1:
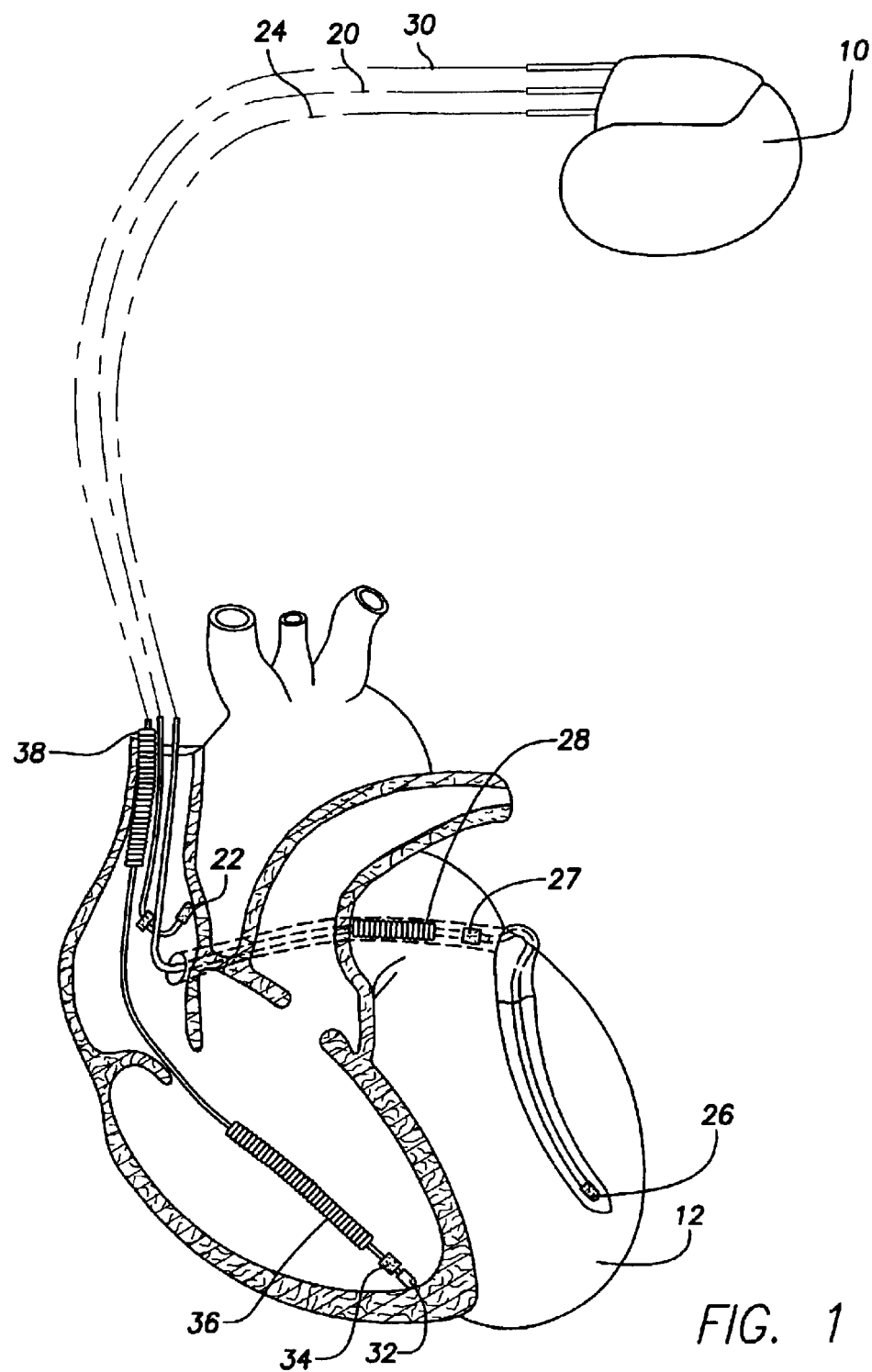
FIG. 1 is a simplified, partly cutaway view illustrating an implantable stimulation device in electrical communication with at least three leads implanted into the heart of a patient for delivering multi-chamber stimulation and shock therapy.

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.
Stimulation Device FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region"

refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
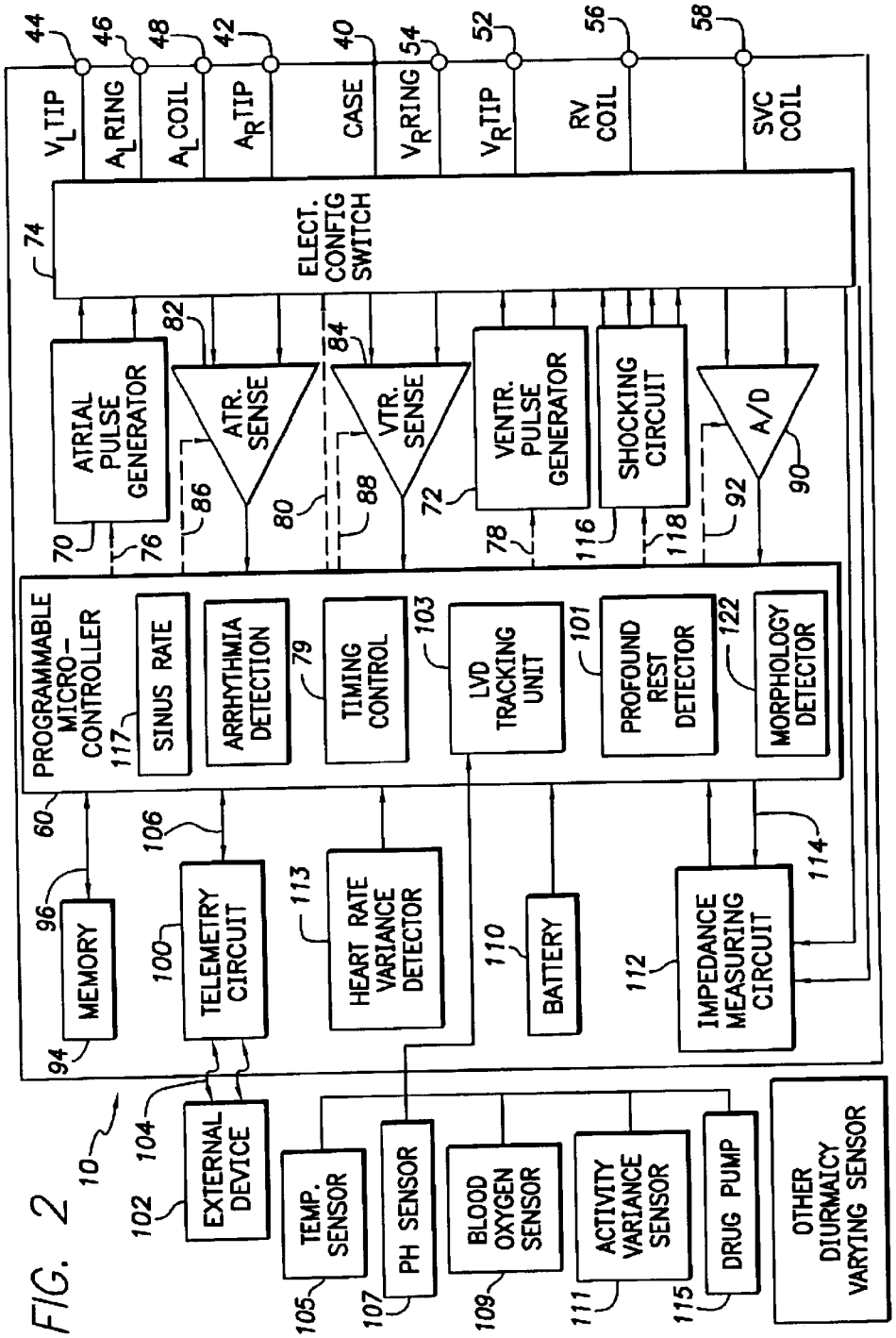
FIG. 2 is a functional block diagram of the multi-chamber implantable stimulation device of FIG. 1, illustrating the basic elements that provide cardioversion, defibrillation and/or pacing stimulation in four chambers of the heart and, in particular, illustrating an LVD tracking unit for automatically tracking the progression or regression of LVD within the patient.

FIG. 2 illustrates a simplified block diagram of the multi-chamber implantable stimulation device 10 which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as a "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the right atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial ring electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry or processor, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, ventricular interconduction (V—V) delay, pacing mode, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the sensing circuits, 82 and 84, preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 12 within each respective tier of therapy. A feature of the stimulation device 10 is the ability to sense and store a relatively large amount of data (e.g., from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

In a preferred embodiment, the stimulation device 10 further includes at least one physiologic sensor for detecting a diurnally-varying physiological parameter of the patient. The following exemplary sensors are shown: a body temperature sensor 105, a pH sensor 107, a blood $O_2$ sensor 109, an activity variance sensor 111, a heart rate variance sensor 113, a QT interval sensor 119, a contractility sensor 121, a stroke volume sensor 123 and a heart wall displacement sensor 125 (for detecting either displacement, velocity or acceleration of the heart wall). A profound rest detector 101 of the microcontroller inputs signals from the various physiological sensors to determine whether the patient is in a state of profound rest, such as sleep, and, if so, measures the sinus rate while at profound rest using a sinus rate detector 117. The profound rest detector may be a conventional sleep detector. An LVD tracking unit 103 of the microcontroller automatically evaluates progression or regression of LVD, if any, within the patient based on the sinus rates measured at profound rest in a manner to be described in greater detail below. An increase in the sinus rate at profound over a period of several weeks or months indicates progression of LVD; whereas a decrease indicates regression. Note that, although many of the sensors are shown as being external to the housing of the stimulation device, selected sensors may instead be mounted therein. Also, typically, only one or two physiological sensors are employed. An entire set of sensors is shown in FIG. 2 primarily for the sake of completeness.

Further information regarding a body temperature sensor for use with an implantable medical device may be found in U.S. Pat. No. 4,436,092 to Cook et al. For a description of an activity variance sensor for detecting the rest or sleep state, see U.S. Pat. No. 5,476,483 to Bornzin et al. and U.S. Pat. No. 6,128,534 to Park et al. For a description of a blood oxygen sensor, see U.S. Pat. No. 5,275,171 to Barcel. For a description of a pH sensor, see U.S. Pat. No. 4,252,124 to Maurer et al. For a description of a heart rate variance sensor, see U.S. Pat. No. 5,042,497 to Shapland. For a description of a heart wall displacement sensor see U.S. Pat. No. 5,480,412 to Mouchawar et al. For a description of a QT interval sensor see U.S. Pat. No. 4,527,568 to Rickards. For a description of a contractility sensor see U.S. Pat. No. 4,759,366 to Callaghan. For a description of a stroke volume sensor see U.S. Pat. No. 4,535,774 to Olsen. Each of the aforementioned patents is incorporated herein by reference.

The LVD tracking unit stores appropriate LVD diagnostic information in memory 94 for subsequent review by a physician via an external programmer 102. Based on the progression of regression of LVD, the physician may then modify LVD drug therapy provided to the patient or may adjust control parameters of the pacemaker. Alternatively, if a drug pump or other drug dispensing device 115 is implanted within the patient for automatically delivering LVD drug therapy, LVD tracking unit 103 controls the drug pump in view of any detected progression or regression of LVD, i.e. the LVD tracking unit 103 increases the dosage of LVD drugs if LVD is progressing and decreases the dosage if LVD is regressing. LVD tracking unit 103 may also be used to verify the efficacy of any LVD drug therapy administered to the patient, whether delivered via the implanted drug pump or otherwise. In one example, the LVD tracking unit evaluates changes in the sinus rate of the patient during periods of profound rest to generate LVD diagnostic information, which is transmitted to an LVD diagnostic unit of the external programmer for display (described below). In another example, the LVD tracking unit merely transmits sinus rate values detected during profound rest to the LVD diagnostic unit of the external programmer, which then evaluates changes in the sinus rate and generates the diagnostic information.

For a description of an implantable drug pump, see U.S. Pat. No. 5,527,344 to Arzbaecher et al., which is incorporated herein by reference. Although described with respect to an implantable drug pump, other similar drug delivery systems for use with patients, such as controllable patches and the like, can alternatively be used. In yet another example, the LVD tracking unit controls the stimulation system to apply stimulation to the heart to alter contractility of the heart.

In addition to aiding in the evaluation of changes in LVD, the aforementioned activity variance sensor or other appropriate sensors may also be employed as a "rate-responsive" sensor for using adjusting pacing stimulation rate according to the exercise state of the patient. Accordingly, microcontroller 60 responds by adjusting the various pacing parameters (such as rate, AV Delay, V—V Delay, etc.) which control how and when the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

In one embodiment, stimulation device 10 operates as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11–40 joules) energy, as controlled by the microcontroller 60. Such shocking pulses are applied to the patient's heart through at least two shocking electrodes, as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (e.g., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of 5–40 joules), delivered asynchronously (since R-waves may be too disorganized) and pertaining exclusively to the treatment of fibrillation. Accordingly, the microcontroller 60 is capable of controlling the synchronous or asynchronous delivery of the shocking pulses.

External Programmer Overview

Figure 3:
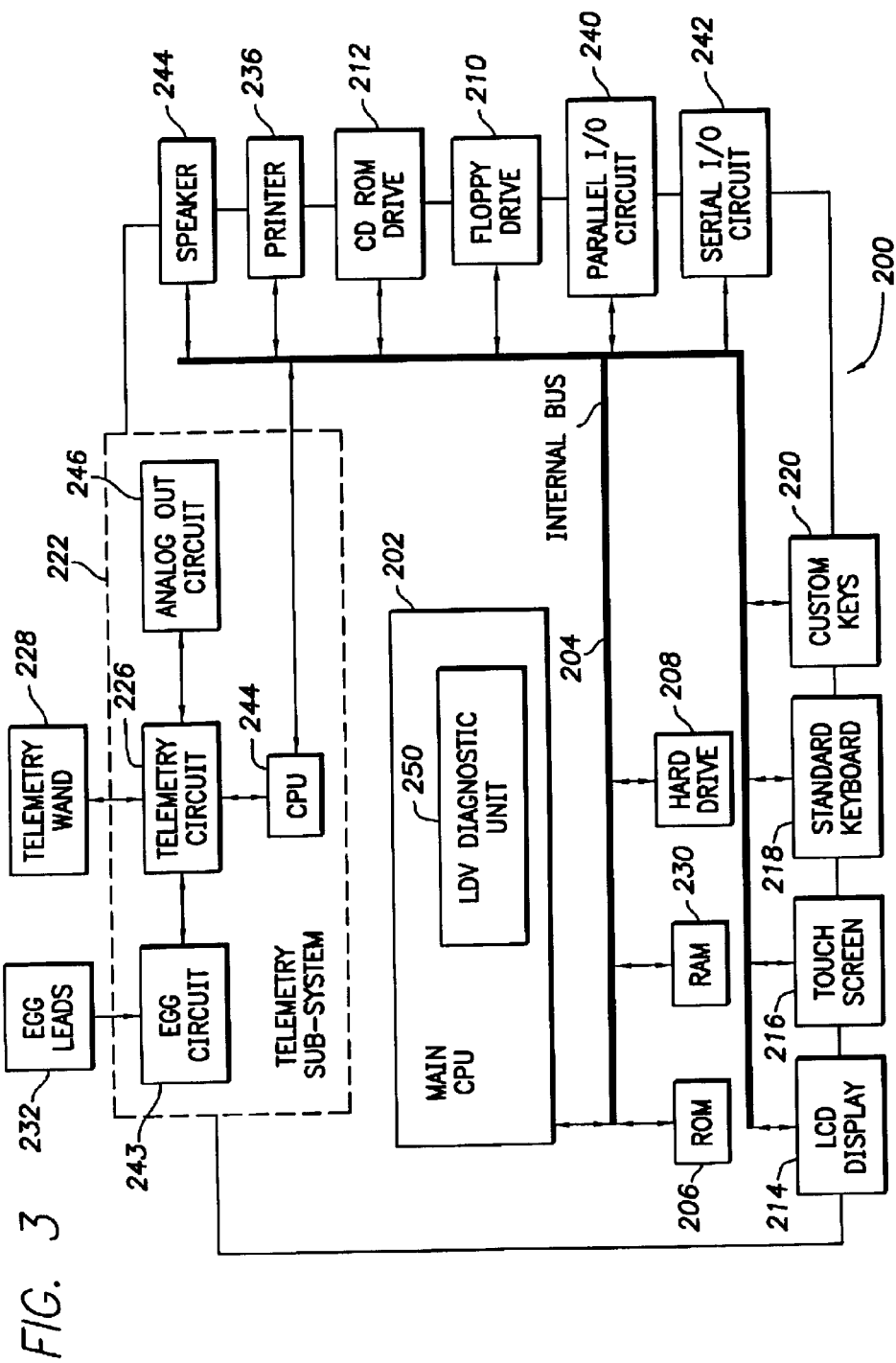
FIG. 3 is a functional block diagram illustrating components of a programmer for use in programming the implantable device of FIG. 1 and in particular illustrating an LVD diagnostic unit for displaying information pertaining to the progression or regression of LVD within the patient.

FIG. 3 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 200 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Prior to reprogramming specific parameters, the physician may control the external programmer to display any or all of the data retrieved from the implanted device or from the ECG leads, including displays of ECGs, IEGMs, and statistical patient information. Any or all of the information displayed by programmer may also be printed using a printer 236.

CPU 202 includes an LVD diagnostic unit 250 for generating and displaying diagnostic information pertaining to the progression or regression of LVD within the patient based on information received from the LVD tracking unit of the implanted device (103 of FIG. 2). In one example, the LVD tracking unit of the implanted device evaluates changes in the sinus rate of the patient during periods of profound rest to generate LVD diagnostic information, which is transmitted to the LVD diagnostic unit for display. In another example, the LVD tracking unit merely transmits sinus rate values detected during profound rest to the LVD diagnostic unit, which then evaluates changes in the sinus rate and generates the diagnostic information. LVD diagnostic unit 250 is described in detail below primarily with reference to FIG. 9.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports might be provided.

A speaker 244 is included for providing audible tones to the user, such as a warning beep in the event the physician provides improper input. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail each and every feature of the hardware and software of the device and is not intended to provide an exhaustive list of the functions performed by the device.

Tracking LVD Using Implantable Device

Figure 4:
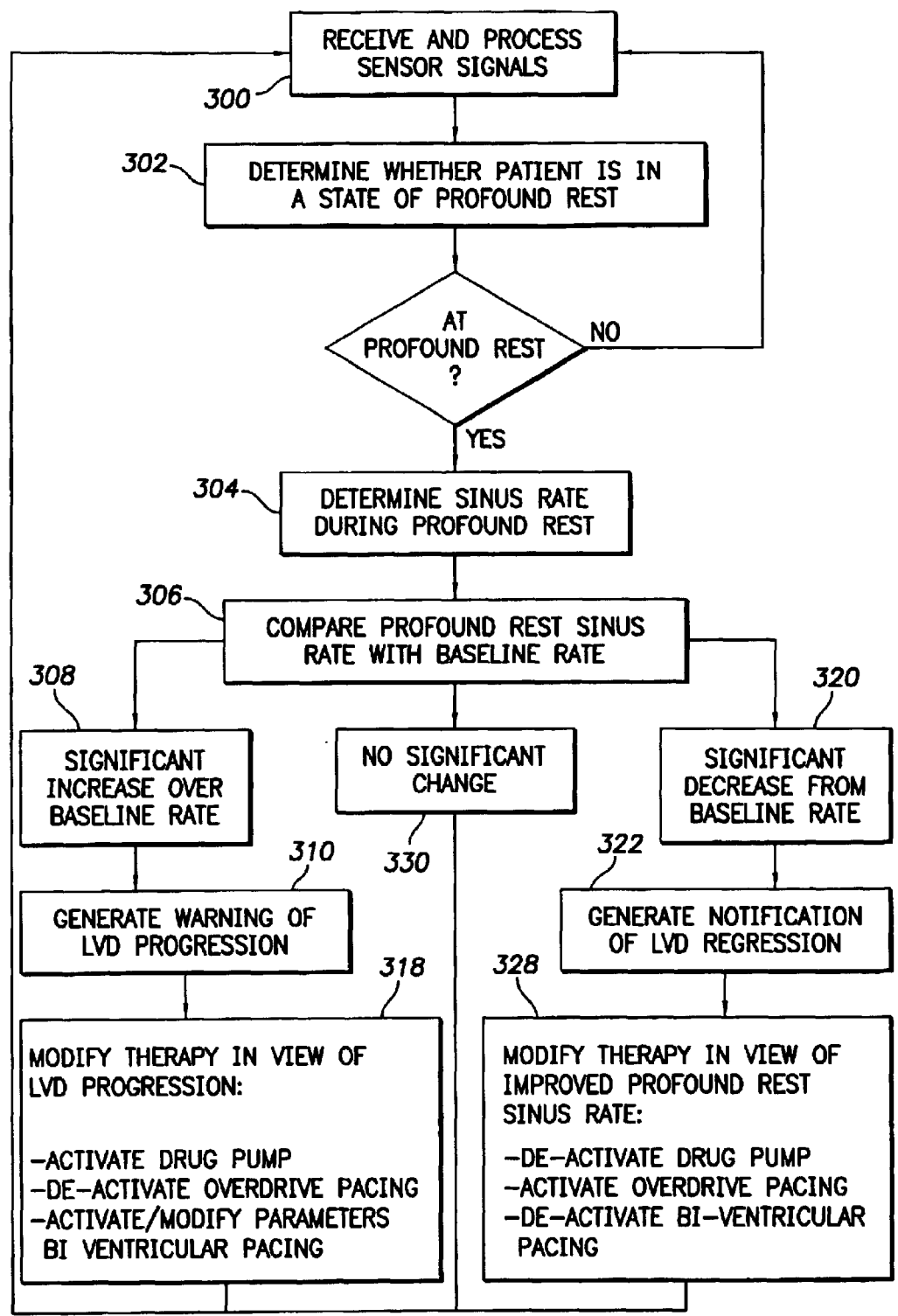
FIG. 4 is a flow chart illustrating a method performed by the LVD tracking unit of FIG. 2 for tracking the progression or regression of LVD.

In FIG. 4, a flow chart is shown describing an overview of the operation and features implemented in one embodiment of the stimulation device 10. In this flow chart and the other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device.

While the implanted device is delivering therapy to the patient under the control of microcontroller 60, LVD tracking unit (unit 103 of FIG. 2) periodically operates to perform the steps of FIG. 4. Initially, at step 300, the LVD tracking unit controls the profound rest detector to input signals from at least one of the various diurnally-varying physiological sensors that may be used with the device, such as body temperature sensor (105), pH sensor (107), blood $O_2$ sensor (109), activity variance sensor (111), heart rate variance detector (113) QT interval sensor (119), contractility sensor (121), stroke volume sensor (123), or heart wall displacement sensor (125). The LVD tracking unit, at step 302, then controls the profound rest detector to determine whether the patient is currently asleep or in any other state of profound rest and, if not, processing merely returns to step 300. Thus, while the patient is awake and active, steps 300 and 302 are merely repeated in a loop. However, once the patient enters a state of profound rest, the LVD tracking unit then proceeds to perform the remaining steps of FIG. 4.

At step 304, the LVD tracking unit determines the sinus rate of the patient while in profound rest using sinus rate detector (117). The sinus rate while asleep or during any other state of profound rest is referred to herein as the "profound rest sinus rate". The profound rest sinus rate is derived from a set of individual sinus rate values detected by the microcontroller and relayed to the LVD tracking unit. Preferably, the LVD tracking unit inputs a predetermined number of individual sinus rate values (e.g. three) each detected during profound rest with each measurement space apart and then averages the individual values to yield a single profound rest sinus rate. In this manner, a single aberrant sinus rate detected during profound rest will not unduly influence operation of the LVD tracking unit. The profound rest sinus rate is stored as diagnostic data in memory along with the current date and time. At step 306, the profound rest sinus rate is compared with a baseline rate, retrieved from memory, to determine if the profound rest sinus rate has significantly changed from the baseline rate.

The baseline rate is a profound rest sinus rate previously detected by the LVD tracking unit and stored within the memory for comparison purposes. The baseline rate typically represents the profound rest sinus rate of the patient at the time the LVD tracking unit became operational within the patient. Assuming the LVD tracking unit was activated when the device was implanted in the patient, the baseline rate represents the first profound rest sinus rate detected following implant, typically the following evening while the patient is asleep. If the LVD tracking unit was not activated until a follow-up session between the patient and physician, the baseline rate then represents the first profound rest sinus rate detected after the follow-up session. Also, during a follow-up session, the physician can control the LVD tracking unit to erase the baseline rate, permitting the system to detect and store a new baseline rate. Preferably, the baseline rate is an average rate determined from some predetermined number of sinus rate measurements taken over a period of several days following activation of the LVD tracking unit, as averaging helps ensure a reliable baseline value. For example, the baseline rate may be an averaged based on the first ten profound rest sinus rate measurements.

If, at step 308, the profound rest sinus rate has been found to significantly exceed the baseline rate, then the LVD tracking unit generates a warning signal at step 310 indicating that LVD has progressed (i.e. worsened) within the patient since the baseline value had been stored. The profound rest sinus rate is deemed to have significantly exceeded the baseline rate if it exceeds a LVD progression threshold value set above the baseline rate. The threshold value may be set to, for example, a value 10%–30% greater than the baseline rate. In any case, the warning signal is stored along with other diagnostic data within the memory of the device for subsequent transmission to an external programmer for review by the physician. At that time, the physician can review the diagnostic data, including the baseline rate and each of the recorded profound rest sinus rates and, if warranted, modify the programming of the device and/or modify drug therapy applied to the patient. If the device is provided with components permitting transmission of warning signals and other data to a bedside monitor, then the LVD warning is immediately transmitted to the bedside monitor, either for notifying the patient or for subsequent transmission to an centralized computing system for notifying the physician. In this manner, the patient and/or physician can be promptly notified of any progression in LVD within the patient, perhaps warranting an immediate follow-up session wherein the physician can review diagnostic data from the device. A system incorporating bedside monitoring units connected to a centralized external programmer system is described in U.S. patent application Ser. No. 09/823,374, "System And Method For Remote Programming Of Implantable Cardiac Stimulation Devices", filed Mar. 29, 2001, and incorporated by reference herein.

At step 318, the LVD tracking unit automatically modifies therapy delivered by the implanted device to the patient in an attempt compensate for the progression in LVD. For example, if the device is connected to an implanted drug pump provided with LVD drugs, the LVD tracking unit controls the drug pump to begin delivering the LVD drugs or, if already delivering such drugs, to increase the dosage. LVD drugs include beta-blockers, angiotensin-converting enzyme inhibitors (ACEIs), diuretics, diltiazem, diltiazem, and angiotensin II antagonists. If the device is currently performing overdrive pacing, particularly in the ventricles, overdrive pacing may be controlled to be less aggressive or may be deactivated entirely. Overdrive pacing is made less aggressive deactivated completely to reduce stress on the heart. A system for overdrive pacing the heart is described in U.S. patent application Ser. No. 09/471,788, "Methods and Apparatus for Overdrive Pacing Heart Tissue Using an Implantable Cardiac Stimulation Device", filed Dec. 23, 1999, an incorporated by reference herein. If the device is configured to perform either single-site pacing in the ventricles or bi-ventricular pacing, the LVD tracking unit controls the device to switch to bi-ventricular pacing from single-site pacing or otherwise modifies bi-ventricular pacing control parameters. Bi-ventricular pacing is activated to reduce stress on the ventricles that may otherwise arise with single-site pacing.

Alternatively or additionally, at step 318, the LVD tracking unit controls the stimulation device to apply stimulation to alter heart contractility. More specifically, if LVD is progressing, stimulation is applied in an effort to increase heart contractility to thereby increase stroke volume so as to prevent the increase in resting sinus rate associated with LVD. A description of a technique for altering heart contractility (also referred to as post-extrasystolic potentiation) is provided in U.S. Pat. No. 5,213,098 of Bennett et al., which is also incorporated herein by reference.

Other adjustments may be made to other pacing control parameters that may help compensate for LVD including rate response control parameters, circadian slopes, max tracking rates, V—V timing, sequence of activation, etc. No attempt is made herein to itemize all possible pacing control parameters that might be controlled in accordance with the general principles of the invention.

If, at step 320, the profound rest sinus rate has been found to have significantly decreased from the baseline rate, then the LVD tracking unit generates a notification signal at step 322 indicating that LVD has regressed (i.e. improved) within the patient since the baseline value had been stored. As in step 308, the determination at step 320 is made using a threshold value set relative to the baseline rate. The LVD regression threshold value may be set to, for example, a value 10%-30% below the baseline rate. The notification signal is stored for subsequent transmission to an external programmer for review by the physician. If warranted, the physician may modify the programming of the device and/or modify drug therapy applied to the patient to reflect the regression in LVD.

At step 328, the LVD tracking unit automatically modifies therapy delivered by the implanted device to the patient in view of the regression in LVD. To this end, the LVD tracking unit controls the drug pump to reduce the dosage of any LVD drugs being delivered to the patient or, if already at a low dosage, to deactivate the drug pump entirely. Alternatively, the LVD tracking unit may activate overdrive pacing or deactivate bi-ventricular pacing, to exploit the improvement in LVD.

Finally with regard to FIG. 4, if no significant change is detected, at step 330, either above or below the baseline value, then the LVD tracking unit merely returns to step 300 to wait for another occurrence of profound rest to repeat the comparison process of steps 306–328. Preferably, the method of FIG. 4 is performed at most only once per day. The method may be triggered based on time of day. For example, the method may be triggered at midnight each night. Three profound rest sinus rates are measured one hour apart (assuming the patient is in a state of profound rest at those times). Following detection of the third profound rest sinus rate value, the three values are averaged and then the comparison process of steps of 306–320 are performed once using the averaged value. In this manner, at most a single new profound rest sinus rest value is detected and stored each night. This helps reduce the amount of diagnostic data stored as well as reduce the amount of processing resources required by the LVD tracking unit.

Thus far, a technique has been described for tracking the progression or regression of LVD and for modifying therapy in response thereto. In the following, a technique for verifying the efficacy of LVD drug therapy is described.

Verification of LVD Drug Efficacy Using Implantable Device

Figure 5:
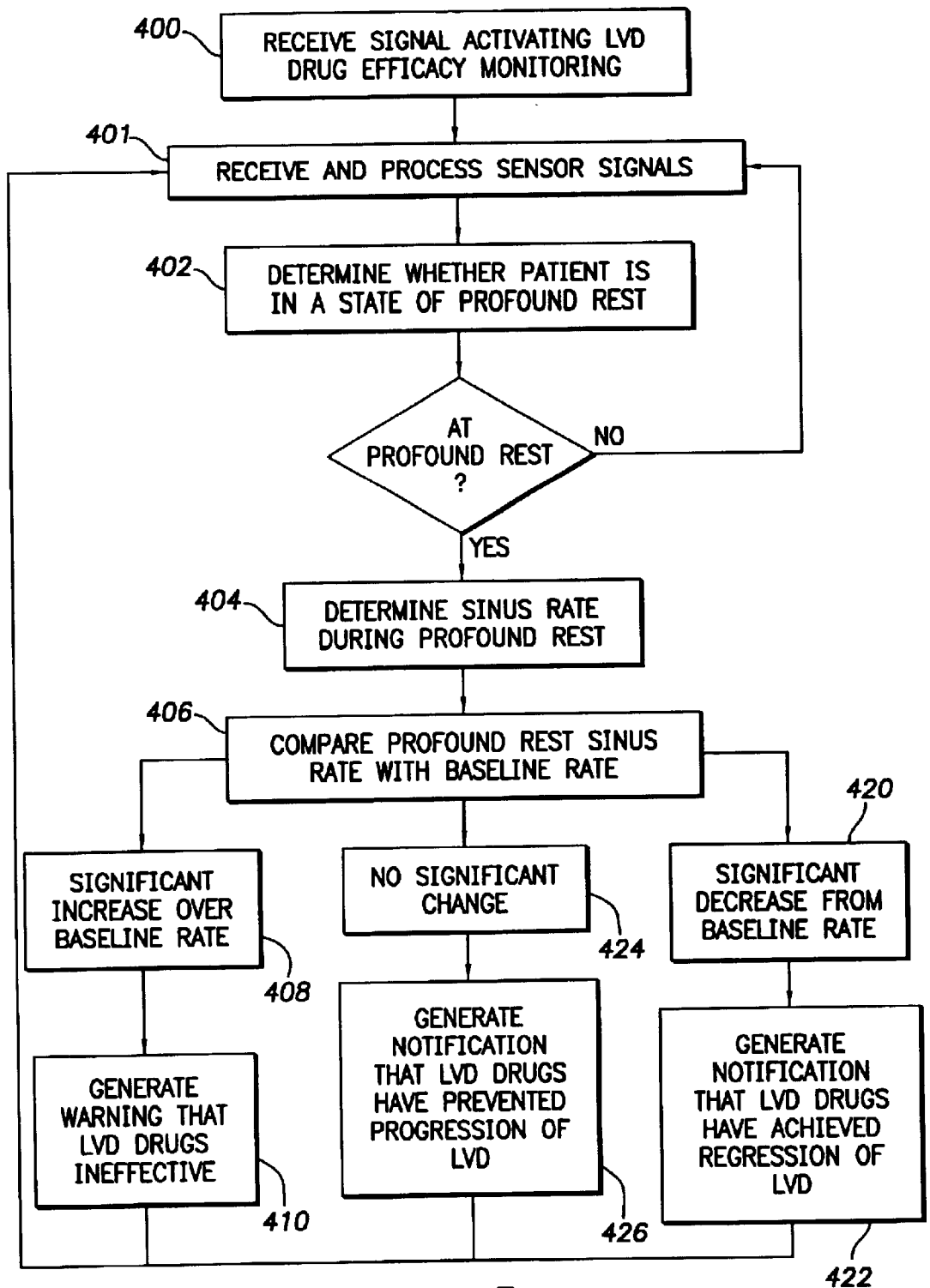
FIG. 5 is a flow diagram illustrating a method performed by the LVD tracking unit of FIG. 2 for verifying the efficacy of LVD drug therapy.

FIG. 5 illustrates a technique for verifying the efficacy of LVD drug therapy. Many of the steps of FIG. 5 are similar to those of FIG. 4 and, accordingly, will not be described again in detail. Initially, upon placing the patient on LVD drug therapy, the physician controls the external programmer to send a signal to the implanted device to notify the device of the drug therapy and to activate the drug efficacy monitoring process. The signal is received from the external programmer at step 400. Then steps 401–406 are periodically performed to determine the sinus rate of the patient at profound rest and to compare the profound rest sinus rate with a pair of threshold rates, above and below the baseline rate. The first profound rest sinus rate measured following activation of the drug efficacy monitoring process is stored as the baseline rate. At that time, the LVD tracking unit calculates an upper threshold indicative of progression of LVD and a lower threshold indicative of regression of the disease. As before, the profound rest sinus rate may be an averaged rate based on at least three measured sinus rates during a single episode of profound rest, typically obtained at night the patient is asleep.

If, at step 408, the profound rest sinus rate has been found to exceed the upper threshold, then the LVD tracking unit generates a warning signal at step 410 indicating that the LVD drug regime has been ineffective in prevent progression of the disease. The warning signal is stored along with other diagnostic data within the memory of the device for subsequent transmission to an external programmer for review by the physician, typically during a follow-up session. The physician may then modify the drug regime, perhaps by prescribing a higher dosage of the drugs or a different set of drugs. Additionally, the physician may wish to reprogram of the device to reflect the failure of the drug regime. As with the technique of FIG. 4, above, overdrive pacing may be programmed to be less aggressive to eliminate stress on the heart or the device may be switched to bi-ventricular pacing. If, at step 420, the profound rest sinus rate has been found to fall below the lower threshold, then the LVD tracking unit generates a notification signal at step 422 indicating that the LVD drug regime has been effective in achieving regression of the LVD. Upon subsequent review, the physician may modify the programming of the device and/or modify drug therapy applied to the patient to reflect the regression in LVD. If, at step 424, the profound rest sinus rate has not changed significantly from the baseline rate, then the LVD tracking unit generates a notification signal at step 516 indicating that the LVD drug regime has been at least effective in preventing further progression of LVD. The physician may then wish to continue the same drug therapy.

Display of LVD Diagnostic Information Using External Programmer

Figure 9:
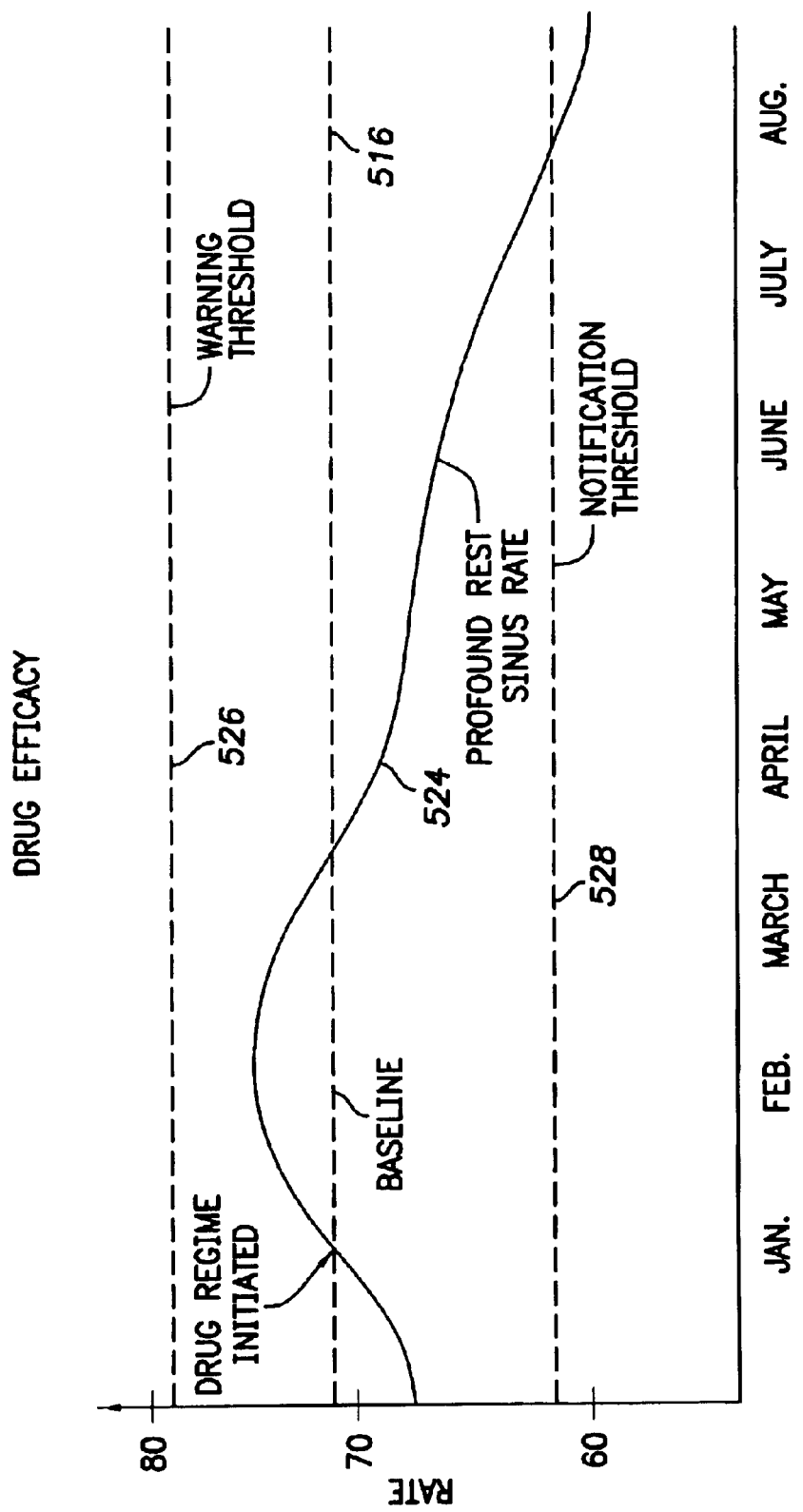
FIG. 9 is a graph generated by the LVD diagnostic unit of FIG. 3 illustrating LVD drug efficacy as a function of time.

As noted, the external programmer of FIG. 3 includes an LVD diagnostic unit 250 for generating and displaying diagnostic information pertaining to the progression or regression of LVD within the patient based on information received from the LVD tracking unit of the implanted device (103 of FIG. 2). Depending upon the implementation, the LVD tracking unit of the implanted device evaluates changes in the sinus rate of the patient during periods of profound rest to generate LVD diagnostic information, which is transmitted to the LVD diagnostic unit for display (FIG. 6) or the LVD tracking unit merely transmits sinus rate values detected during profound rest to the LVD diagnostic unit, which then evaluates changes in the sinus rate and generates and displays LVD diagnostic information (FIG. 9). In both cases, the LVD diagnostic information displayed by the LVD diagnostic unit includes, for example:

warnings, graphs and other information pertaining to the progression or regression of LVD within the patient;

changes to pacing control parameters based on the progression or regression LVD;

changes to drug pump control parameters based on the progression or regression LVD;

warnings, graphs and other information pertaining to the efficacy of LVD drug therapy;

changes to pacing control parameters based on the efficacy of drug therapy; and changes to drug pump control parameters based on the efficacy of drug therapy.

Insofar as pacing and drug pump control parameters are concerned, if the implanted device has already implemented changes to such parameters, the LVD diagnostic unit displays a record of the changes and permits the physician to set forth further changes. If the LVD diagnostic unit of the external programmer is proposing changes to control parameters, the changes are presented as recommendations for the physician to review and modify, if needed. The changes are only forwarded to the implanted device following review by the physician. The operations of the LVD diagnostic unit will be summarized with reference to the remaining figures.

Figure 6:
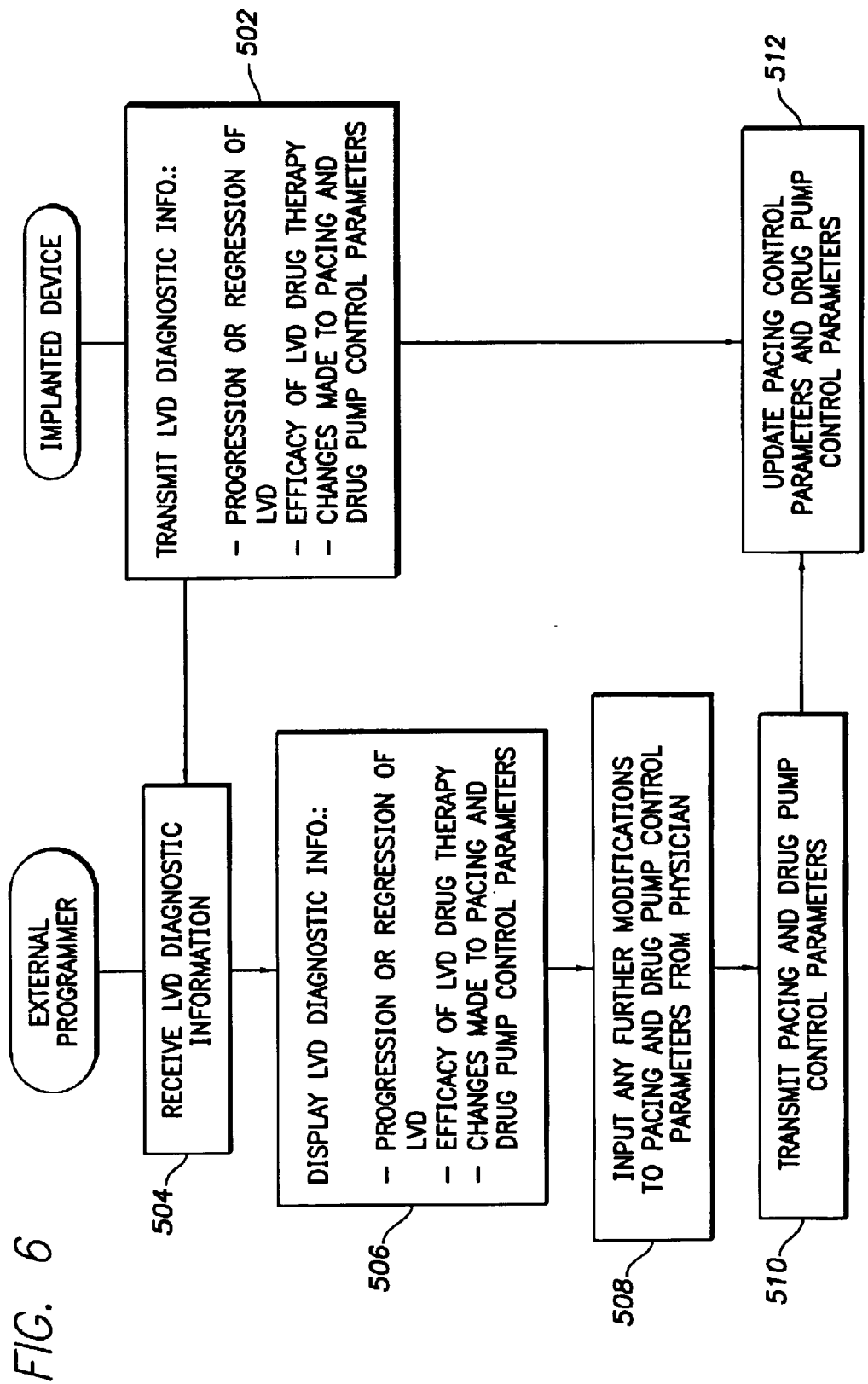
FIG. 6 is a flow chart illustrating a method performed by the LVD diagnostic unit of FIG. 3 for displaying LVD diagnostic information generated by the implanted device of FIG. 2.

FIG. 6 illustrates a technique for displaying LVD diagnostic information received from the implanted device. At step 502, the telemetry unit of the implanted cardiac stimulation device transmits LVD diagnostic information previously generated and recorded by the LVD tracking in accordance with the methods of FIGS. 4–5. LVD diagnostic information can include all of the types of information summarized immediately above. LVD diagnostic information is received by the telemetry unit of external programmer at step 504 and displayed at step 506 under the control of the LVD diagnostic unit.

Figure 7:
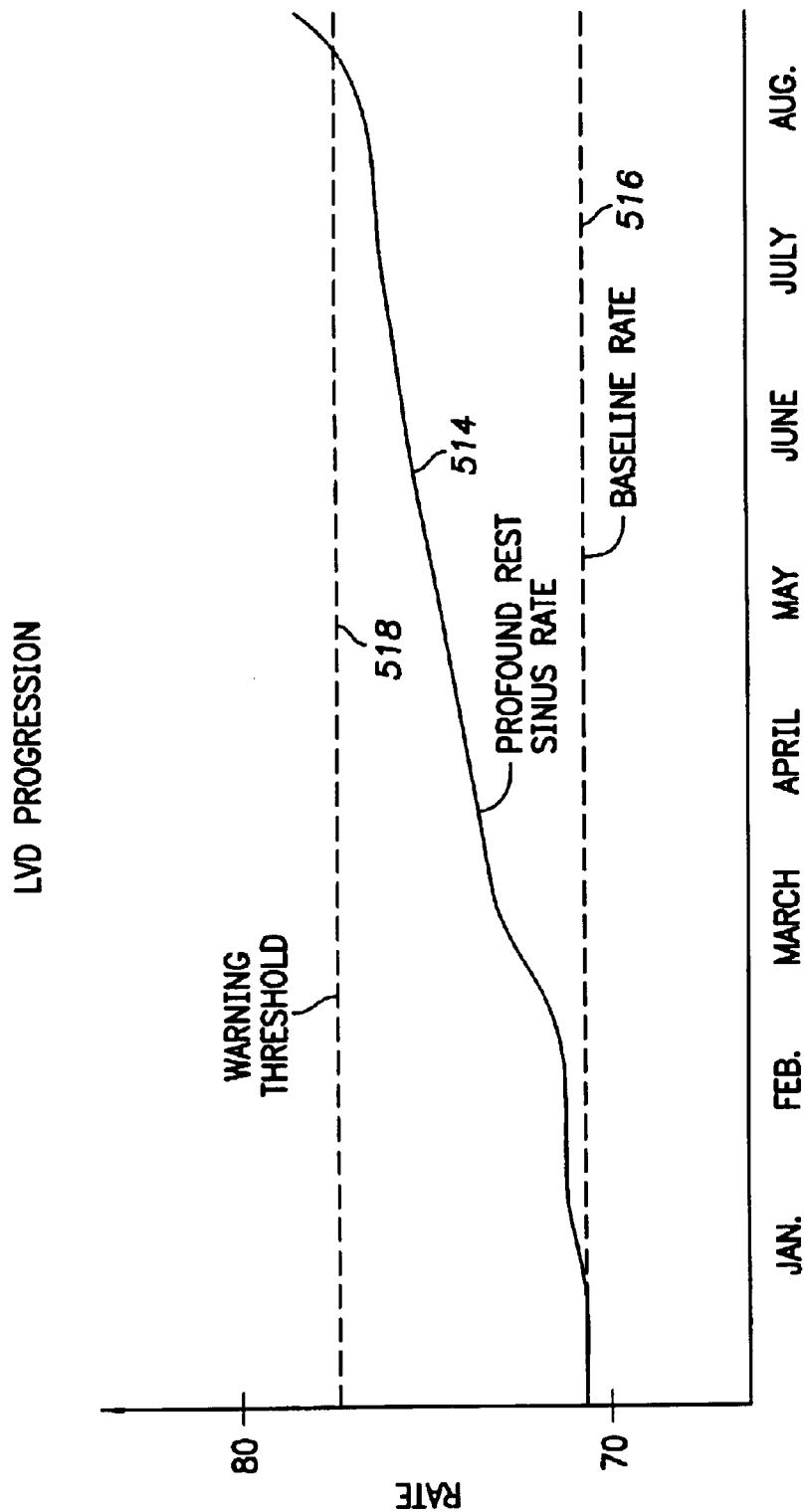
FIG. 7 is an exemplary graph generated by the LVD diagnostic unit of FIG. 3 illustrating LVD progression as a function of time.
Figure 8:
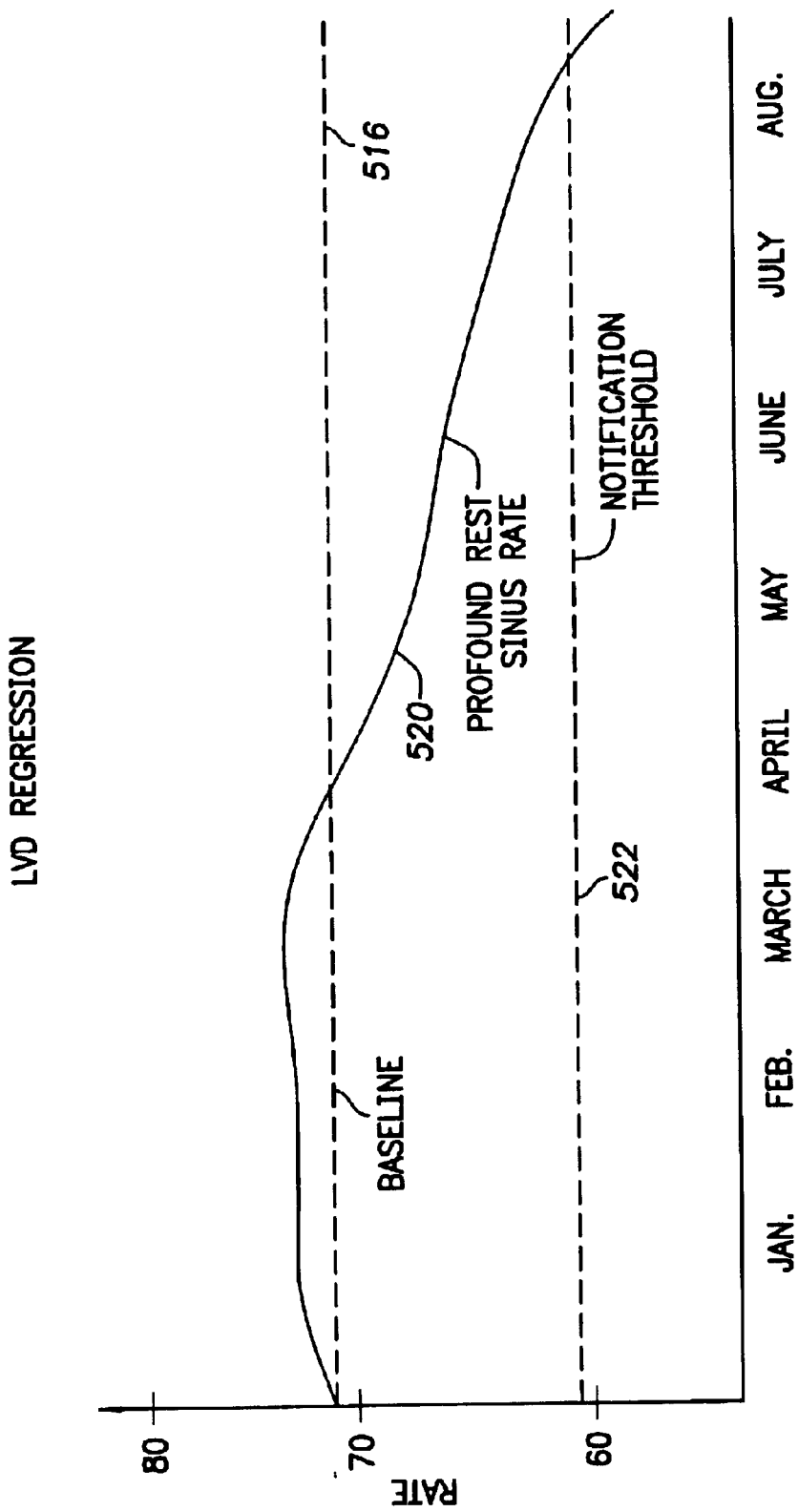
FIG. 8 is a graph generated by the LVD diagnostic unit of FIG. 3 illustrating LVD regression as a function of time.

FIG. 7 illustrates an exemplary graph that may be generated at step 504 by the LVD diagnostic unit, which shows an increase in profound rest sinus rate 514 over a period of several months, indicative of a progression in LVD. The figure also illustrates a baseline rate 516 and a progression threshold rate 518, which is part of the LVD diagnostic information received from the implantable device and is described above in connection with FIG. 4. As can be seen, the recorded profound rest sinus rate remained constant for some time, then increased gradually until it exceeded the threshold rate. FIG. 8 illustrates another exemplary graph that may be generated at step 504, which shows a decrease in profound rest sinus rate 520 over a period of several months, indicative of a regression in LVD. The figure also illustrates the aforementioned baseline rate 516 and a regression threshold rate 522, which is also part of the LVD diagnostic information received from the implantable device. FIG. 9 illustrates yet another exemplary graph that may be generated at step 504, which shows the efficacy of an LVD drug regime. The figure shows a profound rest sinus rate 524 recorded over a period of several months along with the baseline rate 516 and upper and lower drug efficacy threshold rates, 526 and 528, which are part of the LVD diagnostic information received from the implantable device and are described above in connection with FIG. 5. As noted, the baseline rate is the profound rest sinus rate at the time the drug regime was initiated. As can be seen, the profound rest sinus rate initially continues to increase, but eventually the drug regime counteracts LVD and achieves regression, ultimately causing the profound rest sinus rate to fall below the lower threshold.

Thus FIGS. 7–9 provide a few examples of graphs that may be displayed (or printed out) by the LVD diagnostic unit. Although not shown, additional displays or printouts set forth changes to any pacing or drug pump control parameters made by the implanted device. As can be appreciated, a wide range of additional displays and printouts can be generated in accordance with the invention and no attempt is made herein to describe or itemize all such displays or printouts.

Continuing with FIG. 6, at step 508, the LVD diagnostic unit of the external programmer then prompts the physician to provide further modifications to pacing or drug pump control parameters for forwarding to the implanted device at step 510. In this regard, if the implantable device is currently programmed to performing overdrive pacing, particularly in the ventricles, the physician may choose to reprogram the overdrive pacing to be less aggressive or may choose to deactivate overdrive pacing entirely. As another example, if the implantable device is currently programmed to perform single-site pacing in the ventricles, the physician may choose to re-set the device to instead perform bi-ventricular pacing. If the implantable device is connected to a drug pump, the physician may choose to activate the drug pump based on the LVD diagnostic information presented or to adjust the dosage of drugs delivered by the drug pump. Control parameters affecting heart rate contractility may also be adjusted. Any new or modified pacing or drug pump control parameters transmitted by the external device at step 510 are received by the implantable device at step 512 for updating internal control values.

Figure 10:
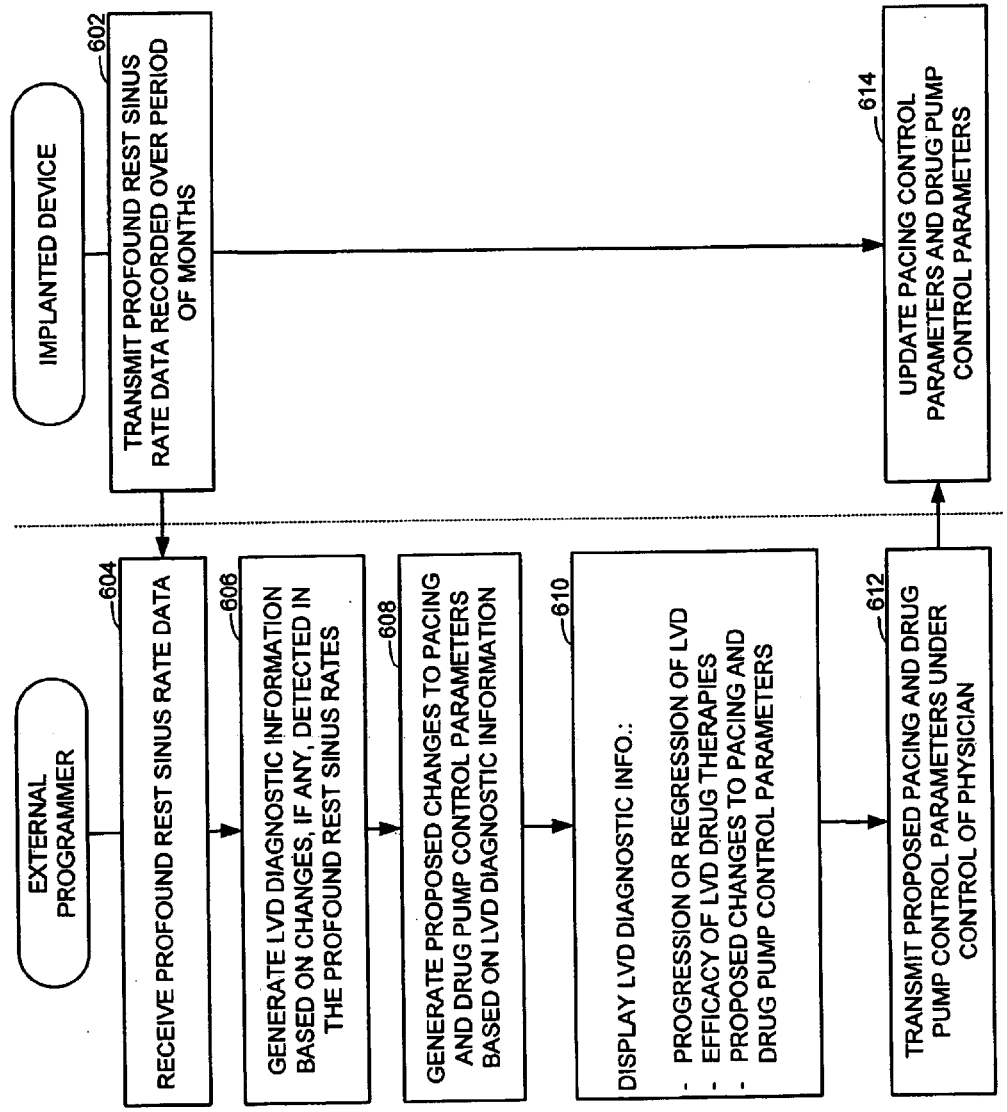
FIG. 10 is a flow chart illustrating a method performed by the LVD diagnostic unit of FIG. 3 for generating LVD diagnostic information based on profound rest sinus rates recorded by the implanted device of FIG. 2.

Thus FIG. 6 sets forth, at a high level, a method for displaying LVD diagnostic information generated by an implanted device. FIG. 10 sets forth a similar method but wherein the implanted device transmits profound rest sinus rates to the external programmer, which actually generates LVD diagnostic information based on the sinus rates. At step 602, the implanted cardiac stimulation device transmits profound rest sinus rates previously measured and recorded by the LVD tracking unit in accordance with the initial steps of method of FIG. 4. The profound rest sinus rate data is received by the external programmer at step 604. The LVD diagnostic unit, at step 606, process the raw sinus rate data to generate the various types of LVD diagnostic information already described including, for example, LVD progression or regression information or LVD drug efficacy information. At step 608, the LVD diagnostic unit then proposes changes to pacing or drug pump control parameters based on the progression or regression of LVD and based on the efficacy of LVD drugs, if any, administered to the patient. Proposed changes to control parameters may be generated, for example, in accordance with the techniques described above with reference to steps 318 and 328 of FIG.4.

LVD diagnostic information and any proposed changes to control parameters are displayed, under the control of the LVD diagnostic unit, at step 610, for review by the physician. At step 610, graphs such as those of FIGS. 7–9 may be presented. The physician then accepts or rejects the proposed changes to the control parameters or makes alternative modifications to the control parameters. Any modified control parameters are then transmitted from the external program to the implanted device at steps 612 and 614.

The foregoing techniques track LVD based on sinus rates detected while the patient is in a state of profound rest as determined by an activity variance sensor or similar sensor. In alternative implementations, LVD is tracked based on sinus rates detected during other states, such as during an exercise state. In one example of the alternative technique, an activity detector, which may include one or more of the physiological sensors described above, detects when the patient has entered an exercise state and the sinus rate of the patient is then measured while the patient is within the exercise state. Multiple sinus rates may be averaged together. LVD is monitored by tracking differences in the exercise-state sinus rate over a period of time. As before, baseline and threshold rates can be used for comparison purposes, appropriate diagnostics information can be generated and displayed, and pacing or drug therapy can be modified based on changes, if any, in sinus rates measured during activity states. Hence, it is contemplated that the exemplary profound rest-based LVD tracking techniques described in detail above (and the corresponding drawings) can be modified as needed to apply to activity state-based LVD tracking techniques as well. In the interests of brevity, a separate set detailed descriptions and drawings covering activity state-based techniques are not provided herein. A combination of profound rest-based tracking techniques and activity state-based tracking techniques can be exploited within a single system.

What have been described are various techniques performed by an implantable cardiac stimulation device for tracking LVD and for controlling the delivery of therapy based on LVD. While the invention has been described with reference to particular embodiments, modifications could be made thereto by those skilled in the art without departing from the spirit and scope of the invention.

What is claimed is:

1. In an implantable cardiac stimulation device having a control unit, a sinus rate detector and a profound rest detector, a method for monitoring left ventricular dysfunction (LVD) within a patient, the method comprising:
    detecting when the patient is in a state of profound rest using the profound rest detector;
    measuring the sinus rate of the patient while the patient is in a state of profound rest using the sinus rate detector;
    tracking changes in LVD, if any, within the patient using the control unit based on changes in the sinus rate measured while at profound rest; and
    adjusting V—V timing of bi-ventricular pacing in response to changes in LVD.

2. The method of claim 1 wherein the device includes a physiological sensor for detecting a diurnally-varying physiological parameter and wherein the profound rest detector determines whether the patient is in a state of profound rest based on signals received from the physiological sensor.

3. The method of claim 2 wherein the physiological sensor is selected from a group of diurnally-varying sensors including a body temperature sensor, pH sensor, a blood $O_2$ sensor, an activity variance sensor, a heart rate variance sensor, a stroke volume sensor, a QT interval sensor, a contractility sensor and a heart wall displacement sensor.

4. In an implantable cardiac stimulation device having a control unit, a sinus rate detector and a profound rest detector, a method for monitoring left ventricular dysfunction (LVD) within a patient, the method comprising:
    detecting when the patient is in a state of profound rest using the profound rest detector;
    measuring the sinus rate of the patient while the patient is in a state of profound rest using the sinus rate detector;
    tracking changes in LVD, if any, within the patient using the control unit based on changes in the sinus rate measured while at profound rest;
    recording a baseline sinus rate detected while in an initial state of profound rest;
    comparing the baseline rate with a subsequent sinus rate detected while in a subsequent state of profound rest; and
    determining whether the subsequent sinus rate exceeds the baseline rate by a predetermined margin and, if so, generating a signal indicative of progression of LVD within the patient.

5. The method of claim 1 wherein the step of tracking changes in LVD include the steps of:
    recording a baseline sinus rate detected while in an initial state of profound rest;
    comparing the baseline rate with a subsequent sinus rate detected while in a subsequent state of profound rest; and
    determining whether the subsequent rate is less than the baseline rate by a predetermined margin and, if so, generating a signal indicative of regression of LVD within the patient.

6. The method of claim 1 wherein the step of tracking changes in LVD include the steps of:
    recording a baseline sinus rate detected while in an initial state of profound rest;
    comparing the baseline rate with a subsequent sinus rate detected while in a subsequent state of profound rest; and
    determining whether the subsequent rate is between predetermined upper and lower margins bracketing the baseline rate and, if so, generating a signal indicative of a lack of significant change in LVD within the patient.

7. The method of claim 1 wherein the implantable cardiac stimulation device includes a system for delivering cardiac therapy and wherein the method further includes the step of:
    modifying therapy delivered to the patient based on changes, if any, in LVD.

8. The method of claim 7 wherein the device is capable of bi-ventricular pacing and single-site pacing and wherein the step of modifying therapy delivered to the patient includes the step of:
    switching from single-site pacing to bi-ventricular pacing if progression in LVD is detected.

9. The method of claim 7 wherein the step of modifying therapy delivered to the patient includes the step of:
    applying stimulus to alter heart contractility.

10. The method of claim 7 wherein the implantable cardiac stimulation device includes a drug dispensing device for delivering LVD drugs to the patient and wherein the step of modifying therapy delivered to the patient includes the step of: controlling the drug dispensing device based on the changes, if any, in LVD.

11. The method of claim 1 further including the step of:
    verifying LVD drug efficacy based on the changes, if any, in LVD.

12. The method of claim 11 wherein the step of verifying LVD drug efficacy include the steps of:
    recording a baseline profound rest sinus rate detected while the patient is receiving LVD drugs;
    comparing the baseline rate with a subsequent sinus rate detected while in a subsequent state of profound rest and while the patient is still receiving the dosage of LVD drugs; and
    determining whether the subsequent rate is less than the baseline rate by a predetermined margin and, if so, generating a signal indicating that the LVD drugs have been effective.

13. The method of claim 1 wherein the implantable cardiac stimulation device includes a telemetry device for transmitting signals to an external device and wherein the method includes the additional step of:
    transmitting signals representative of changes in LVD, if any, to the external device.

14. The method of claim 13 wherein the step of transmitting signals representative of changes in LVD, if any, includes the steps of: transmitting values representative of sinus rates detected while in a state of profound rest as measured over the period of time.

15. In an implantable cardiac stimulation device, a system for monitoring left ventricular dysfunction (LVD) within a patient comprising:
- a profound rest detector operative to determine when the patient is in a state of profound rest;
- a sinus rate detector operative to measure the sinus rate of the patient while the patient is in a state of profound rest;
- an LVD tracking unit operative to track changes in LVD, if any, within the patient based on changes in the sinus rate measured while at profound rest; and
- a controller adapted to adjust V—V timing of bi-ventricular pacing in response to changes in LVD.

16. The system of claim 15 wherein the device includes a physiological sensor for detecting a diurnally-varying physiological parameter and wherein the profound rest detector is operative to determine whether the patient is in a state of profound rest based on signals received from the physiological sensor.

17. The system of claim 16 wherein the physiological sensor is selected from a group including a body temperature sensor, pH sensor, a blood $O_2$ sensor, an activity variance sensor, a heart rate variance sensor a stroke volume sensor, a QT interval sensor, a contractility sensor and a heart wall displacement sensor.

18. The system of claim 15 wherein the implantable cardiac stimulation device includes a system for delivering cardiac therapy and wherein the system for monitoring LVD is also operative to control therapy delivered to the patient based on changes, if any, in LVD.

19. The system of claim 18 wherein the implantable cardiac stimulation device includes a drug dispensing device for delivering LVD drugs to the patient and wherein the system for monitoring LVD is also operative to control the drug dispensing device based on the changes, if any, in LVD.

20. The system of claim 15 wherein the system for monitoring LVD is also operative to verify LVD drug efficacy based on the changes, if any, in LVD.

21. The system of claim 15 wherein the implantable cardiac stimulation device includes a telemetry device for transmitting signals to an external device and wherein the system for monitoring LVD is also operative to control the telemetry device to transmit signals representative of changes in LVD, if any, to the external device.

22. A system for monitoring left ventricular dysfunction (LVD) within a patient, the system comprising:
- means for measuring the sinus rate of the patient while in a state of profound rest;
- means for tracking changes in LVD, if any, within the patient based on changes in the sinus rate measured while at profound rest; and
- means for adjusting V—V timing of bi-ventricular pacing in response to chances in LVD.

23. A method for monitoring left ventricular dysfunction (LVD) within a patient, an implantable cardiac stimulation device performing a method comprising:
- detecting when the patient is in a predetermined activity state;
- measuring the sinus rate of the patient while the patient in the predetermined activity state; and
- tracking changes in LVD, if any, within the patient based on changes in the sinus rate measured while in the predetermined activity state.

24. In an implantable cardiac stimulation device, a system for monitoring left ventricular dysfunction (LVD) within a patient comprising:
- an activity detector operative to determine when the patient is in a predetermined activity state;
- a sinus rate detector operative to measure the sinus rate of the patient while the patient is in the predetermined activity state; and
- an LVD tracking unit operative to track changes in LVD, if any, within the patient based on changes in the sinus rate measured while in the predetermined activity state.

* * * * *